United States Patent [19]
Feres

[11] Patent Number: 5,425,849
[45] Date of Patent: Jun. 20, 1995

[54] FILM-TYPE EVAPORATOR

[76] Inventor: Vaclav Feres, 3002 Buena Vida Cir., Las Cruces, N. Mex. 88001

[21] Appl. No.: 865,340

[22] Filed: Apr. 8, 1992

[30] Foreign Application Priority Data

Apr. 11, 1991 [DE] Germany .................. 41 11 753.0

[51] Int. Cl.[6] ............................................. B01D 1/22
[52] U.S. Cl. ........................................ 159/6.1; 159/6.2;
 159/13.1; 159/49; 159/901; 202/197; 202/236;
 165/914
[58] Field of Search ............. 159/DIG. 40, 6.1, 49,
 159/62, 25.1, 25.2, 901, 13.1; 165/109.1, 108,
 DIG. 914; 202/197, 236; 203/40, 89

[56] References Cited

U.S. PATENT DOCUMENTS

| 2,927,634 | 3/1960 | Gudheim | 159/6.1 |
|---|---|---|---|
| 3,098,718 | 7/1963 | Ferrari | 202/238 |
| 3,229,384 | 1/1966 | Goulston | 202/238 |
| 3,590,916 | 7/1971 | Mutzenberg et al. | 159/6.2 |
| 3,654,981 | 4/1972 | Aitchison | 159/6.1 |
| 3,678,983 | 7/1972 | Widmer et al. | 159/6.2 |
| 3,851,404 | 12/1974 | Fracke et al. | 159/6.1 |
| 3,921,709 | 11/1975 | Feres | 159/6.1 |
| 3,926,588 | 12/1975 | Speece | 55/52 |
| 4,054,485 | 10/1977 | Linder et al. | 159/6.2 |
| 4,073,696 | 2/1978 | Müller | 165/108 |
| 4,193,837 | 3/1980 | Wyss et al. | 159/6.2 |
| 4,335,079 | 6/1982 | Vander Mey | 159/6.1 |
| 4,410,337 | 10/1983 | Gallichsen et al. | 55/52 |
| 4,440,595 | 4/1984 | Broberg | 159/13.1 |
| 4,683,026 | 7/1987 | Feres | 159/13.1 |
| 4,780,178 | 10/1988 | Yoshida et al. | 202/238 |
| 4,981,554 | 1/1991 | Loconpolo et al. | 202/237 |

FOREIGN PATENT DOCUMENTS

| 0583014 | 9/1959 | Canada | 159/6.1 |
|---|---|---|---|
| 2134803 | 8/1984 | United Kingdom | 159/6.1 |
| 0285887 | 11/1970 | U.S.S.R. | 159/6.1 |

Primary Examiner—Virginia Manoharan
Attorney, Agent, or Firm—Antonelli, Terry, Stout & Kraus

[57] ABSTRACT

A film-type evaporator has an upright container, a heating system arranged on the outside of its jacket, a rotor rotating in the container and an upper part with a vapor chamber and droplet separator. In the upper area of the rotor the product is fed onto the inner container wall and runs down in the form of a thin film in which evaporation takes place. Circulation evaporation with a high thickening capacity is made possible in that the container has an unheated lower part constructed as a receiving flask in which the product is collected and a central part with the heating system, on whose inner wall film-type evaporation takes place, and in that the tubular rotor extends into the lower part and is constructed as a circulating pump, which delivers the product from the lower part on the inside of the tubular rotor into its upper area and centrifugally delivers it there to the inner wall of the central part.

15 Claims, 5 Drawing Sheets

FILM-TYPE EVAPORATOR

FIELD OF THE INVENTION

The invention relates to a film-type evaporator with an upright container, a heating system externally located on its casing, a rotor rotating in the container and a vapor chamber with droplet separation located above the rotor in an upper part of the container, the product being fed onto the inner wall of the container in the upper area of the rotor and runs down as a thin film in which evaporation takes place and the concentrate is drawn off from the base of the container.

BACKGROUND OF THE INVENTION

Numerous different film-type evaporator constructions are known and are characterized in that the product to be thickened or evaporated runs, in the form of a film-like layer, over the evaporation surface, which leads to high k-values (heat transfer coefficients). A uniform film thickness over the entire evaporation length can be achieved in that the rotor has ledges with wiper edges, which move past the inner wall at a limited distance therefrom. Film-type evaporators are particularly suitable for the concentration, thickening or distillation of heat-sensitive products, e.g. liquid or liquid/solid mixtures.

Such film-type evaporators operate in a single-pass process, that is, the starting product is only passed once over the evaporating surface and the concentrate produced is drawn off. High efficiency levels during thickening and/or better separating effects can be obtained only by adopting a multistage construction, in that either several evaporators are connected in series or several evaporating surfaces are arranged in step-like manner in a single container and the concentrate is transferred from one evaporating surface to the other. The multistage arrangement in the case of such film-type evaporators either leads to high space requirements or to considerable sizes, so that such evaporating plants are only suitable for a large-scale use.

In, for example, U.S. Pat. No. 2,927,634, a lower film-type evaporator in a lower part of a container thereof, is provided with a rotating rotor with radially extending blade-like ledges, which form the wiper or wiping edges. The container is conically constructed in the lower part and the wiper edges are correspondingly inclined and at a limited distance from the container inner wall. As a result the starting product introduced into the container at the upper end of the rotor and which runs down the inner container wall is uniformly distributed in thin film form. Concentrate is drawn off at the bottom of the lower part. Even with type of evaporator the thickening efficiency is limited as a result of the single pass. An increase in the thickening capacity can only be achieved by increasing the overall height.

SUMMARY OF THE INVENTION

The aim of the invention is to provide a small evaporator which has a high thickening capacity and treats the product in a careful manner.

According to the present invention a film-type evaporator is provided wherein the container has an unheated lower part constructed as a receiving flask into which the product collects, and a central part having the heating system. Film type type evaporation takes place along the central part and a tubular rotor extends in the lower part near to the bottom of the container and is constructed as a circulating pump, with the pump delivering the product from the lower part on the inside of the tubular rotor into its upper area and delivers it there centrifugally to the inner wall of the central part.

The film-type evaporator according to the invention has a container, which is subdivided into three portions, namely an upper part with a droplet separator for the vapors, a heated central part and a lower part serving as a receiving flask for the product and from which the product is continuously supplied to the central part by the rotating rotor, which simultaneously functions as a circulating pump, so as to be further concentrated by thin film evaporation. In the case of the invention, it is therefore a film-type evaporator with internal product circulation. As a result of the film-type evaporation a careful, but at the same time effective evaporation takes place. As a result of the short contact time between the product and the heating surface a careful treatment occurs. As a result of the circulation principle used by the present invention, despite the careful treatment, high thickening efficiencies can be achieved.

It is advantageous in the construction according to the invention, if the tubular rotor is externally provided with ledges which, substantially parallel to the inner container wall and at a limited distance therefrom have wiper edges. This always ensures that the product runs out in the form of a uniform thin, turbulent film in the vicinity of the heated central part.

According to a preferred construction, at least on the upper part of its axial length, the rotor is constructed as a conically widening tube from the bottom to the top. This portion of the rotor acts directly as a circulating pump, because the product reaching its inside is subject to a centrifugal force and, due to its conicity, also a vertical delivery component, so that, at the upper end of the rotor, the product can be centrifugally delivered to the inner container wall.

For this purpose, at its upper end the tubular rotor is drawn inwards and has below it outlets for the product rising on its inside.

The drawing in of the tubular rotor at the upper end constitutes a flow obstacle for the rising product, so that it passes centrifugally to the outside through the outlets located directly below it and is sprayed onto the inner container wall. Any product which may be reflected on the inner wall is taken up by the rotor ledges and accelerated to the outside again, which ensures that the product runs down the inner container wall.

In its lower inner area the tubular rotor can have conveying members working as a pump, for example, a screw pump, which is immersed in the product located in the lower part and delivers the product to the conical portion of the rotor. However, instead of these conveying members or in addition thereto, over its entire axial length the rotor can be made conical from bottom to top, so that delivery takes place solely as a result of this conicity and the rotation of the rotor.

Another advantageous construction is characterized in that the tubular rotor has, in its casing, above the liquid level in the lower part, openings for the passage of vapors through the rotor, with the openings being surrounded by a collar projecting into the rotor and which ensures that the liquid rising upwards on the inside cannot pass to the outside through the said openings.

In the aforementioned construction the rising vapors not only travel past the outside of the rotor in the upwards direction, but can also be drawn upwards through the interior of the upwardly open rotor.

According to a preferred embodiment the rotor forms on its lower open end a valve seat for a valve body mounted in rotary manner on a valve rod located outside the rotor. By adjusting the valve body the liquid quantity sucked by the rotor from the lower part can be controlled or the liquid supply can be completely cut off, in order to temporarily interrupt the liquid circulation with the rotor rotating.

According to another advantageous embodiment, the rotor is surrounded in its lower area by a concentric, conical tube, which is connected in non-rotary manner thereto, whose lower end is immersed in the product and which, on its inside, delivers upwardly conveyed product to the inner container wall. The external, concentric and conical tube, which rotates with the rotor, also acts as a circulating pump. As a result of its shorter construction, a circulating pump is obtained with two different delivery heads and this can be utilized in the manner described hereinafter.

According to one alternative, the upper end of the tube surrounding the rotor is located below the heated central part and delivers the product to the unheated container wall. In this case the outer tube acts solely as a circulating pump for the product, i.e. ensures homogeneous mixing in the lower part of the container.

Another alternative is characterized in that the upper end of the tube surrounding the rotor is positioned in the vicinity of the heated central part and delivers the product to the heated inner wall of the container.

In this case the two different pump delivery heads are utilized for supplying the product to the heated surface at different levels, so that once again the evaporation capacity is increased.

In the last-mentioned variant not only the tubular rotor, but also the tube externally surrounding it have the ledges forming the wiper edges, so that also in the lower portion of the central part a uniform, thin film formation is ensured. The ledges also ensure that the reflected product is again centrifuged onto the heated inner wall.

According to a further development of the invention the rotor extends into the upper part of the container and has in the upper part a corotating flow baffle for the vapors and which acts as a droplet separator. The flow baffle can be constructed as a disk or circular disk around which the vapors are deflected. It is also possible to superimpose several circular disks, so that the vapor is forced to flow round the said disk from the inside to the outside or form the outside to the inside.

The feedline supplying the starting product to the container can be introduced from below into the tubular rotor and can deliver the starting product to the conical inside of the rotor. The starting product is then conveyed upwards on the inside and sprayed onto the inner container wall. Instead of this, the feedline can also be introduced from above into the container and deliver the starting product to a surface rotating with the rotor, from which it is then passed centrifugally to the outside onto the inner wall of the heated central part.

Preferably, the rotor with its drive shaft is mounted in a detachable cover of the container and, following the release of the latter, can be removed from the container so as to permit the problem-free cleaning and/or replacement of all the functional and rotating parts. It is also possible to subsequently reequip any container by the installation of a rotor and a heating means so as to give a film-type evaporator with product circulation.

Finally, the rotor drive shaft can be supported by a loose step bearing on the container bottom, which is a vibration-stiff construction to the rotor, even in the case of high speeds.

BRIEF DESCRIPTION OF THE DRAWINGS

The invention is described in greater detail hereinafter relative to non-limitative embodiments in connection with the accompanying drawings, wherein.

DETAILED DESCRIPTION

Figure 1:
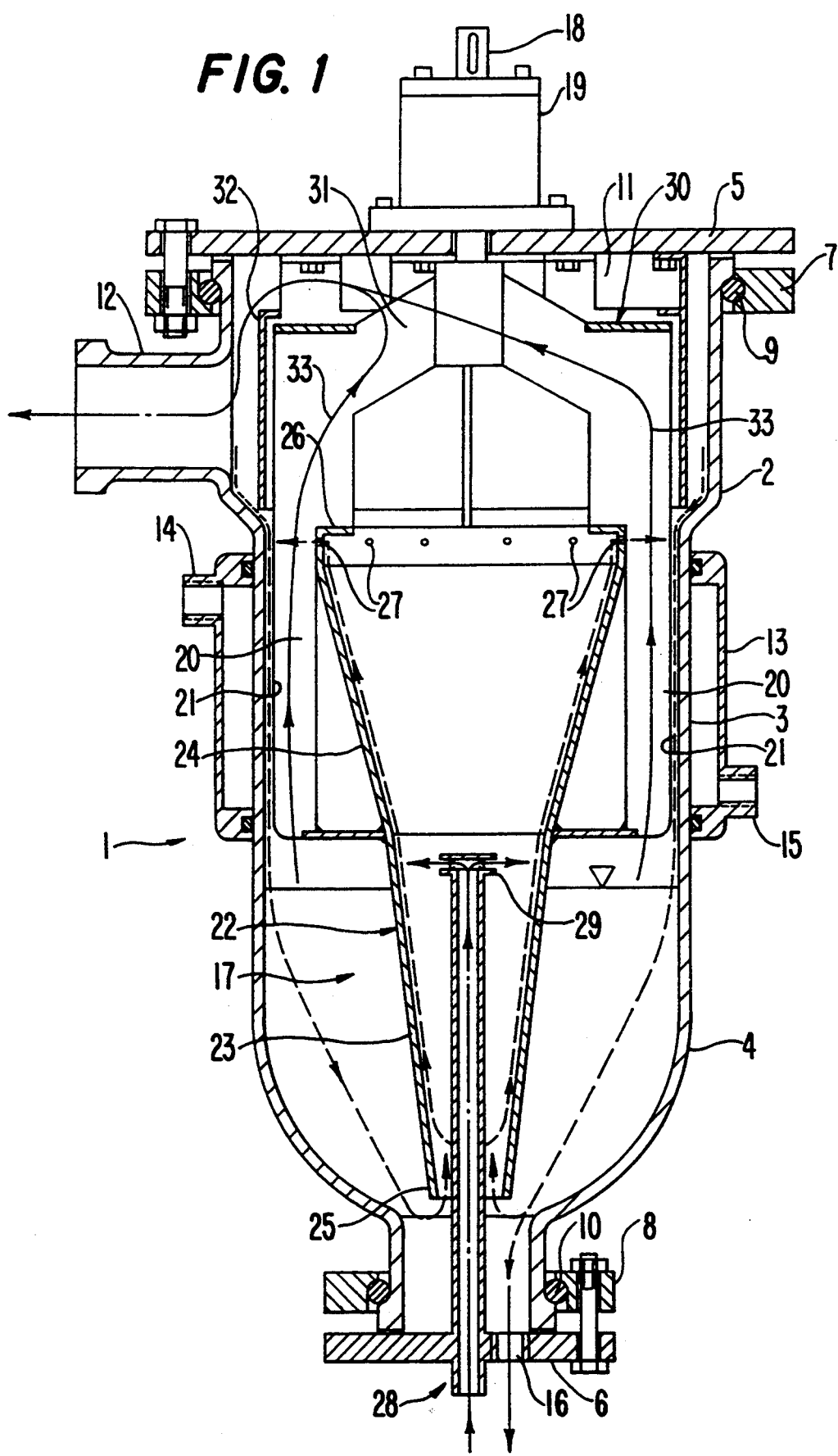
FIG. 1 is a longitudinal cross-sectional view of a first embodiment of the present invention provided with a single-stage circulating pump.

The film-type evaporator according to FIG. 1 has an upright, substantially cylindrical vertically axial container 1 comprising an upper part 2, a central part 3 and a lower part 4 produced in one piece, for example, from glass. At a top thereof, the container 1 is closed by a detachable cover 5 and at a bottom thereof by a detachable base 6, which are, in each case, fixed by engaged ring flanges 7, 8 and interposed seals 9, 10 to the top two or bottom four. The upper part forms a vapor chamber 11 for the vapors to be drawn off by a connection 12. The central part 3 is externally surrounded by a heating jacket 13, through which, for example, flows a liquid or vaporous heat carrier and, for this purpose, has a feed connection 14 and a discharge connection 15. The lower part 4 essentially serves as a receiving flask in which is collected the product or concentrate, and which can be continuously or discontinuously drawn off by a drain 16.

Within the container 1 is placed a rotor 17, which is driven by a drive shaft 18 mounted in vapor-tight manner in a bearing box 19 and which is passed through the cover 5. The rotor 17 is provided on its outside with several ledges 20, which are substantially axially parallel and also radially directed and which form on the outside wiper or wiping edges 21; however, it is not always necessary to provide the ledges 20 with the wiper edges. They ensure a uniform, thick film formation and a turbulent film flow. In all the embodiments, the rotor extends axially over the container central part 3 and projects close to the bottom of the lower part 4, i.e. is immersed in the product collected there.

The rotor 17 serves as a circulating pump. For this purpose it is constructed as a conical tube 22 and, according to FIG. 1, comprises a lower conical portion 23 and an upper conical portion 24 with a larger opening angle than the lower portion 23. The tube 22 is open at its lower end 25, so that at this end, it suctions in the product collected in the lower part 4, which rises upwards on the inner wall of the tube 22 as indicated by the directional arrows. At the upper end of the tube 22, the product is drawn inwards at 26 and is provided directly below the same with outlets 27, so that the rising product is centrifugally sprayed by the outlets 27.

By a feedline 28, which is introduced from below into the rotor 17, supply of the starting product takes place. The feedline 28 ends in the central area of the rotor 17, so that, by a distributor plate 29, the product is centrifugally sprayed onto the inner wall of the tube 22 and is conveyed in an upward direction as a result of the tube conicity.

In its upper region the rotor has a droplet separator 30, which is constructed as a circular disk. The circular disc is fixed to support arms 31, which carry the entire rotor 17. Finally, in the upper part 2, the rotor is surrounded by a type of hood 32, which, in conjunction with the droplet separator 30, leads to a pronounced deflection of the vapors and therefore to an effective droplet separation.

The starting product is supplied by the feedline 28 and is delivered to the inside of the tubular rotor 17, from where the product rises in an upward direction on the conical inner wall and is fed by the outlet 27 onto the container inner wall in the vicinity of the central part 3. On the container inner wall the product flows downwardly in a film-like manner and the ledges 20 with the wiper edges 21, as a result of the circulation thereof, ensure a uniform thin film. Evaporation takes place in thin Film form with the heating jacket 13 in the vicinity of the central part. The concentrated product runs into the untreated lower part 4 and is suctioned in at the upper end 25 of the tube 22 and then transferred upwardly again.

The resulting vapors escape in the upward direction 33, flow round the circular droplet separator 30 and, after further deflection, pass into the waste-steam line 12.

The evaporator shown in FIG. 1 can be operated continuously or discontinuously. When operated discontinuously, the drain 16 is closed and the quantity required for one cycle is supplied by the feed line 28. The drain 16 is kept closed until the desired concentration is reached in the receiving flask 4. In the case of a continuous operation, the quantity drawn off by the drain 16 is compensated by an excess of the quantity of the starting product which excess corresponds to the evaporation rate so that the quantity of liquid circulating within the evaporator remains constant.

It is also pointed out that the conical construction of the rotor 17, particularly in the upper portion 24, leads to a flash evaporation, which permits venting, degassing or defoaming in the upper portion. The entire rotor 17 with all the rotating parts 20 to 27, 30 and 31, as well as the hood 32, can be removed in an upward direction from the container 1 following the release of the cover 5, so that cleaning or repairs can easily be carried out.

Figure 2:
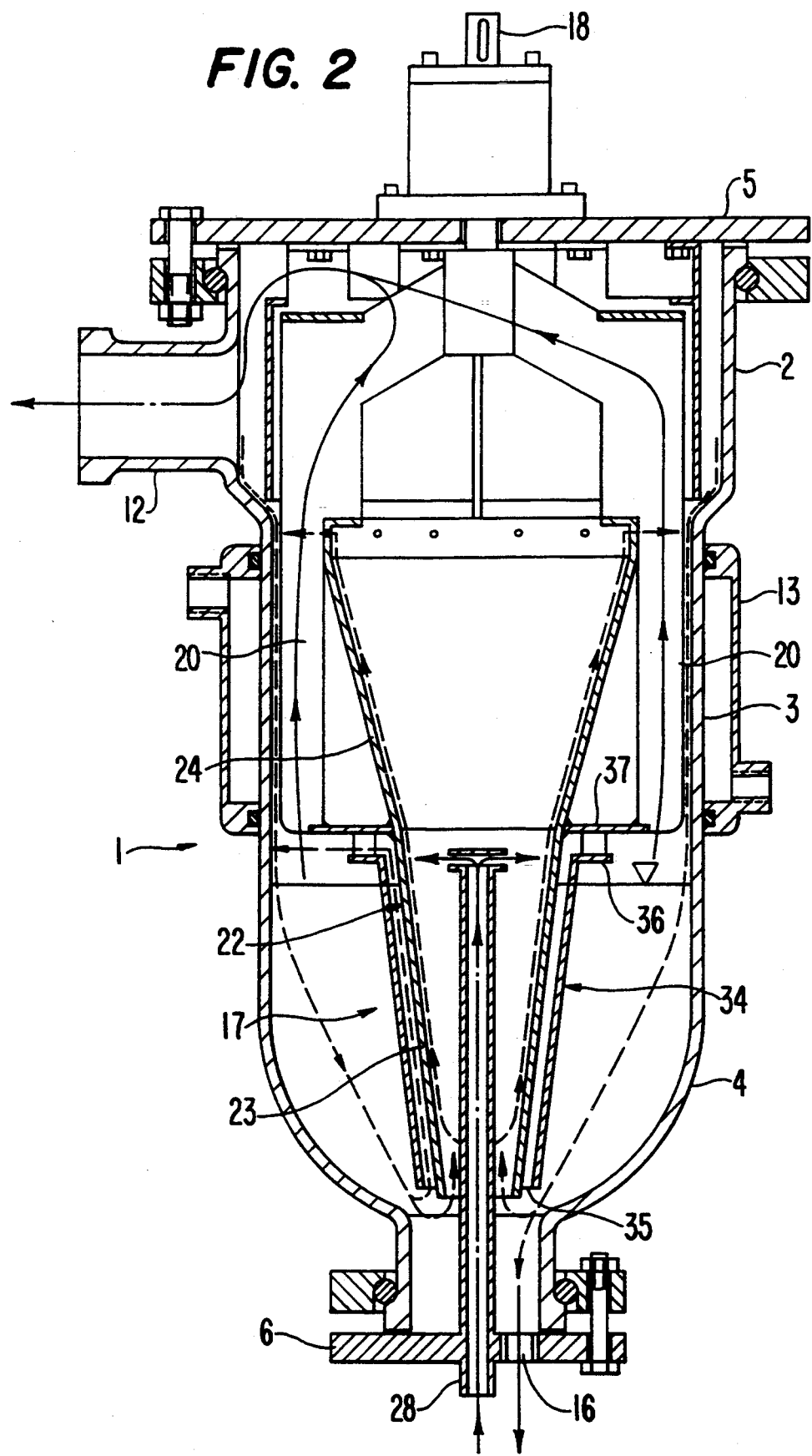
FIG. 2 is a longitudinal cross-sectional view of another embodiment of the present invention with a double acting circulating pump.

The embodiment of FIG. 2 differs from that of FIG. 1 only in that the rotor 17 is surrounded by a further conical tube 34 in the vicinity of the lower conical portion 23 of the tube 22 and which at its lower end 35 is also open and is made shorter in the axial direction. At its upper end the conical tube 34 has a flange 36, with which it is fixed to a ring 37, which connects the ledges 20 at the lower end. Thereby, a two-stage circulating pump is formed, where part of the product in the lower part 4 is suctioned up by the tube 34 at the open end 35 and is transported upwardly; whereas, another part of the product is suctioned up by the lower portion 23 of the tube 22 of the rotor 17, is transported upwardly and sprayed onto the inner wall of the central part 3, with the product, by the tube 34 passing outwardly under centrifugal action in the vicinity of the flange 36 and is sprayed there onto the unheated inner wall of the lower part 4. This part of the product is merely circulated within the lower part 4, so that the product is always homogenized and degassed there.

Figure 3:
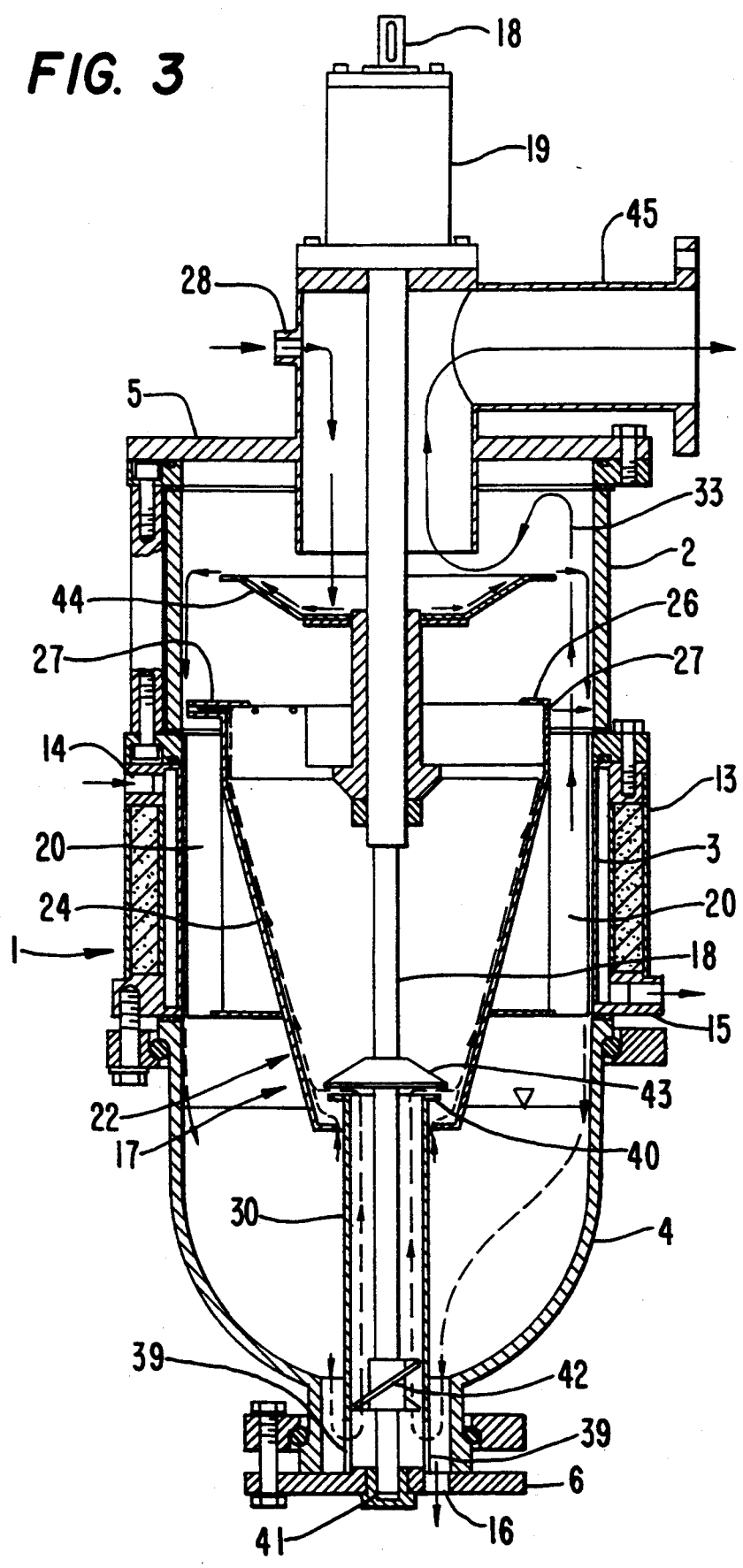
FIG. 3 is a longitudinal cross-sectional view of a further embodiment constructed in accordance with the present invention including a screw pump.

In the embodiment of FIG. 3, the rotor 17 once again comprises a tube 22 with a conical portion 24, which is open at the bottom. A cylindrical tube 38 projects into tube 38 being the tube 22 projects from below with the cylindrical fixed to the detachable base 6 of the lower part 4. Close to the bottom, the tube 38 has feed openings 39 for the product collecting in the lower part 4. At the upper end the tube 38 is provided with a flange 40. The drive shaft is passed downwardly through the entire container 1 and is supported on the bottom of the lower part in a loose bearing 41. In the vicinity of the lower end and close to the feed openings 39 a conveying member in the form of a screw pump 42, is located on the drive shaft 18 which suctions the product in via the feed opening 39 and transports the product upwardly in the tube 38. Immediately above the flange 40 of the tube 38 a guide member 43 is placed on the drive shaft 18 and, in conjunction with the flange 40, deflects the rising product outwardly onto the inner wall of the conical portion 24 of the tube 22, so that the product rises upwardly on the inner wall and is once again sprayed via the outlets onto the inner wall of the central part 3. The starting product is supplied from above by the feed line 28, passes onto a disk rotating with the drive shaft 18 or the rotor 17, which accelerates the starting product outwardly and delivers the product to the inner wall of the upper part 2. From there the starting product passes into the heated central part 3, where the product undergoes a first evaporation. In the embodiment of FIG. 3, the central part 3 is made from steel and is surrounded by an insulated heating jacket; whereas, the lower part 4 and upper part 2 are made from glass.

The conical portion 24 of the tube 22 is provided at its open end with an annular clearance, the conical portion 24 can fulfill an additional feed function and can directly suction a partial quantity of the product in the lower part 4.

In the embodiment according to FIG. 3 the rotating disk 44 simultaneously serves as a flow baffle and, therefore, as a droplet separator for the vapors rising in accordance with the arrow 33, which are in this case drawn off centrally by the cover 5 and a tubular connection 45.

Figure 4:
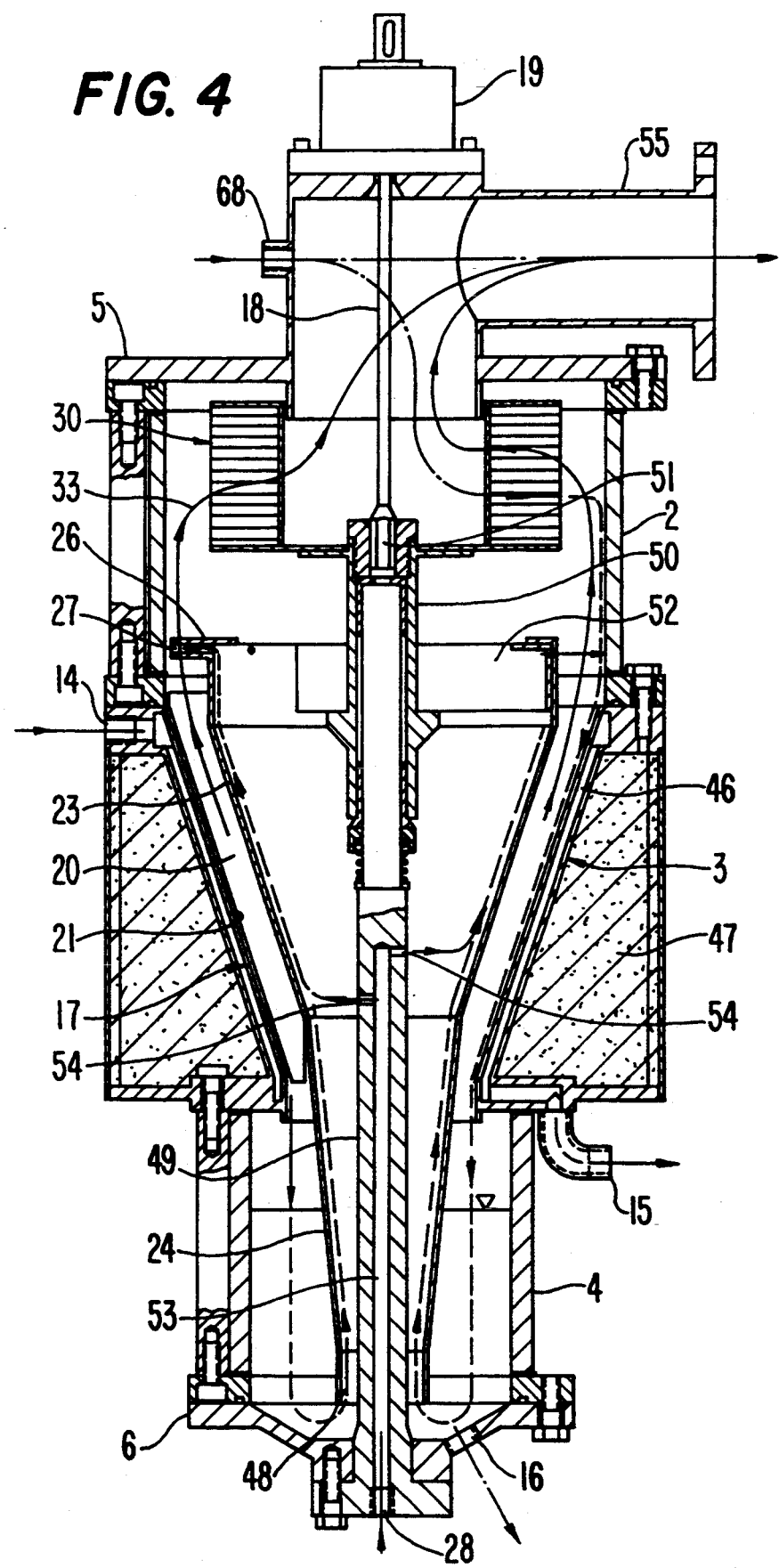
FIG. 4 is a longitudinal cross-sectional view of yet another embodiment of the present invention with an axially supported drive shaft for the rotor.

FIG. 4 shows an embodiment, such as is particularly provided for operation with heating steam. The central part 3 is formed by a double-walled steel jacket, whose area 46 forms the heating chamber surrounded by thick insulation 47. It is connected by a feed 14 to a heating steam source, while the condensate is drawn off by the drain 15. The central part 3 of the container is conical, which takes advantageous account of the evaporation rate. Corresponding to the conicity, the ledges 20 with the wiper edges 21 on the rotor 17 are also conical. The rotor 17 again comprises a tube with an upper conical portion 23 and a lower conical portion 24. In the lower end of the rotor 17 are inserted blades 48 for forming a screw pump.

Within the container 1 is provided a support 49 fixed to the bottom 6, with the support 49 extending axially upwardly through the lower part 4 and the central part 3 and, in the upper area of the support 49, a hollow shaft 50 engages over the support 49 and for the shaft 50 the support 49 forms a loose axial step bearing. The hollow shaft 50 is coupled in axially detachable, but non-rotary manner by a profile 51 to the drive shaft 18. The rotor 17 is fixed by ribs 52 to the hollow shaft 50. The support 49 has an axial bore 53, which serves as a feedline and, in a vicinity of the upper conical portion 23 of the rotor 17, has radial bores 54 which are axially spaced from one another. The starting product supplied by the bore 53 is passed centrifugally outwardly by the bores 54 onto the inner wall of the conical portion 23 and from there is conveyed upwardly so as to once again be sprayed outwardly through the outlets 27.

In this embodiment the droplet separator 30 is formed by a stack of parallel circular disks, which are connected, as a pack, to the hollow shaft 50 and therefore to the drive shaft 18 with which they consequently rotate. The rising vapors pass through the stacked circular disks of the droplet separator 30 into the waste-steam connection 55. This droplet separator can also be in the form of wire lattices, gauzes or the like. Such a droplet separator is also suitable as an additional rectifying stage, as described in conjunction with FIG. 6.

Figures 5, 6:
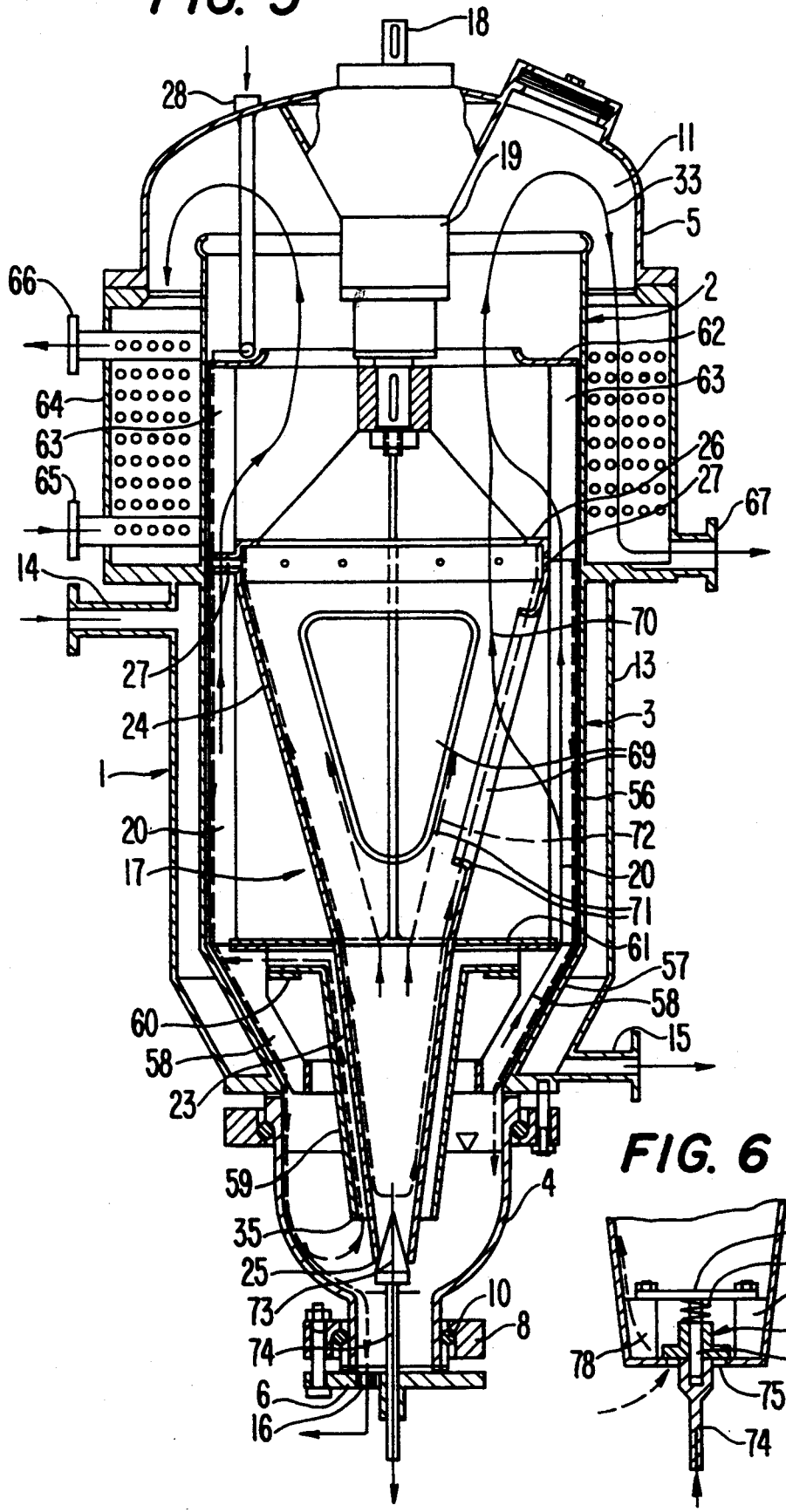
FIG. 5 is a longitudinal cross-sectional view of another embodiment of the present invention with a two-stage circulating pump in an evaporating section.
FIG. 6 is a partial longitudinal cross-sectional view of a lower end of the rotor in a further embodiment of the present invention.

The film-type evaporator according to FIG. 5 is made From steel in its upper part 2 and central part 3; whereas, the lower part 4 is made from glass. The central part 3 comprises a cylindrical portion 56 and a lower, conical portion 57, which, in each case, form the evaporating surfaces and are surrounded by the heating jacket 13. Heating takes place with heating steam, which is supplied by the connection 14, while the condensate is drawn off by the drain 15. The rotor 17 comprises an upper, conical tubular portion 24 and a lower, conical tubular portion 23. In the vicinity of the conical tubular portion 24 the ledges 20 are axially parallel and therefore parallel to the cylindrical portion 26 of the central part 3; whereas, in the lower portion 57 of the central part 3, the ledges 58 are connected with a corresponding parallel angular position to the rotor 17 or a conical tube 59, which concentrically surrounds the conical tubular portion 23 and acts as the second stage of the circulating pump. The conical tube 59 comprises, at its upper end, a flange 60 acting as a run-off surface for the liquid and is connected at a distance from a flange 61 of the rotor 17, which connects the ledges 20 at the lower end thereof. Both the conical tubular portion 23 of the rotor 17 and also the conical tube 59 surrounding the latter suction the product collecting in the lower part 4 in accordance with the directional arrows and transport it upwardly. The upper end or the flange 60 of the tube 59 terminates in the vicinity of the central part 3, so that the product conveyed upwardly by the conical tube 59 is sprayed onto the lower heated portion 57 of the central part 3 and once again runs downwardly as a thin film, supported by the rotating ledges 58. Thus, despite the evaporation rate, in a particularly advantageous and simple manner a uniform film formation is achieved over the entire axial extension of the central part 3.

In the embodiment according to FIG. 5 the feedline 28 is again introduced from above into the container 1. The feed line 28 has its discharge end above a circular disk 62 rotating with the rotor 17, with the rotor 17 accelerating the starting product outwardly and spraying the product onto the inner wall of the upper part 1. Here again the rotor has axially parallel ledges 63, which in the vicinity of the upper part ensure a film-like draining of the starting product on the inner container wall. The disk 62 simultaneously serves as a droplet separator for the vapors rising in accordance with arrow 33.

In the vicinity of its upper part the container 1 is surrounded by a condenser 64, to which the cooling medium is supplied by a feed 65 and is drawn off by the drain 66. In the condenser 64 the vapors are condensed and drawn off as distillate via the drain 67, to which can be connected a vacuum pump. The distillate can also be wholly or partly returned to the upper part 2 of the container 1, as shown in connection with the embodiment of FIG. 4 with the aid of the feed connection 68. The distillate is then passed in countercurrent manner through the droplet separator 30 over the stacked disks, so that a material exchange takes place between the vapors and the distillate. In this case the droplet separator also serves as the rectifying stage.

In order to improve vapor removal, the casing of the rotor 17 has openings 69, through which the vapors rising from below can be drawn off at the top through the interior of the rotor, as indicated by the directional arrows 70. The openings have an inwardly projecting collar 71, so that the liquid rising in the rotor 17, in the manner indicated by the arrow 72, is deflected past the opening 69.

Here again the cover 5 is detachably fixed to the upper part 2 or the condenser 64 surrounding it. The bearing box 19 for the drive shaft 18 is located on the cover 5, so that the entire rotor 17 with all the moving parts can be removed upwardly from the container 1 following the detachment of the cover.

The lower open end 25 of the rotor 17 is constructed as a valve seat with which cooperates a valve body 73 constructed as a cone. The valve body 73 is mounted in rotary manner on a valve rod, guided in a non-rotary, but axially displaceable manner in the bottom 6 of the lower part 4 of the container 1. The gap between the conical valve body 73 and the edge of the opening 25 can be adjusted by regulating the valve rod, in order to regulate or interrupt the liquid quantity suctioned. The valve body can rotate with the rotor in the closed position.

In FIG. 6 the valve body 73 is positioned within the rotor 17, whose lower end 25 is drawn inwards and has an axial opening 75. The valve body is under the action of a spring 76, which urges it into the closed position. For this purpose it is displaceably and rotatably placed on a bolt 77 of a valve rod 74, which is axially displaceable, but not rotatable, so that the valve body 73 can be raised against spring tension. In the lower area of the rotor 17 there are once again conveying members in the form of plates 78, which act as a pump. A ledge 79 is threadably attached opposite plates is, with the ledge 79 supporting the spring.

I claim:

1. A film-type evaporator for evaporating a product comprising:
   an upright container;
   an externally located heating system provided at a central part of the container for causing film-type evaporation at an inside of the central part of the container to produce concentrated product;
   a tubular rotor rotatably mounted in the container which includes means for delivering the product from a lower interior part of the tubular rotor to an upper interior part of the tubular rotor and centrifugally outward from the tubular rotor to an inner wall of an upper part of the container disposed radially outside the tubular rotor and above the central part and the product running down as a thin film past the central part of the container to a flask formed between a lower part of the container and the lower interior part of the rotor where the product collects without any heating and flows into the lower interior part of the rotor immersing into the product to produce recirculation;

means for drawing off concentrated product from the flask;

ledges provided on an external portion of the tubular rotor and extending substantially parallel to the inner wall of the container; and wherein the ledges are provided with wiper edge spaced from the inner wall of the container.

2. A film-type evaporator according to claim 1 wherein:

at least an upper interior part of the tubular rotor is conical and the tubular rotor widens from the interior lower part to the upper part.

3. A film-type evaporator according to claim 1 wherein:

the tubular rotor has an inward extension at the upper interior part and the upper part comprises outlets below the inward extension of the upper interior part for causing the product rising on the interior of the tubular rotor at the upper interior part to be sprayed outwardly.

4. A film-type evaporator according to claim 1 wherein:

conveying members are provided at the lower interior part of the tubular rotor.

5. A film-type evaporator according to claim 1 wherein:

a valve seat is provided at a lower end of the tubular rotor for accommodating a valve body; and the valve body is rotatably mounted on a valve rod guided outside of the tubular rotor.

6. A film-type evaporator according to claim 1 wherein:

openings are provided in the tubular rotor above a product level in the lower interior part for enabling a passage of vapors through the tubular rotor; and the openings are surrounded by a collar projecting into the tubular rotor.

7. A film-type evaporator according to claim 1 wherein:

the tubular rotor is surrounded by a concentric conical tube connected to the lower part of the tubular rotor; and a lower end of the conical tube is immersed in the product and conveys the product upward on an inside wall of the conical tube and delivers the product to the inner wall of the container.

8. A film-type evaporator according to claim 7 wherein:

an upper end of the conical tube is located below the central part and delivers the product to an unheated inner wall of the lower part of the container.

9. A film-type evaporator according to claim 7 wherein:

an upper end of the conical tube surrounding the rotor is located adjacent the central part of the container and delivers the product to a heated inner wall of the central part of the container.

10. A film-type evaporator according to claim 9 wherein:

the conical tube surrounding the rotor is externally provided with ledges forming a wiper edge.

11. A film-type evaporator according to claim 1 wherein:

the tubular rotor extends into the upper part of the container and in the upper part of the container the tubular rotor has a co-rotating flow baffle for vapors of the product with the co-rotating flow baffle acting as a droplet separator.

12. A film-type evaporator according to claim 1 further comprising:

a feedline for supplying the product extending from below the tubular rotor into the tubular rotor and which delivers the product to a conical interior of the tubular rotor.

13. A film-type evaporator according to claim 1 comprising:

a feedline extending from above the container for supplying the product into the container and to a surface rotating with the tubular rotor.

14. A film-type evaporator according to claim 1 further comprising:

a detachable drive shaft of the rotor which is removable from the container,

15. A film-type evaporator according to claim 1 wherein:

a drive shaft of the tubular rotor is supported by a step bearing on the bottom of the container.

* * * * *